US 6,692,725 B2

(12) United States Patent
Endo

(10) Patent No.: US 6,692,725 B2
(45) Date of Patent: Feb. 17, 2004

(54) COMPOSITION FOR ORAL CARE

(75) Inventor: Toshio Endo, Kuba (JP)

(73) Assignee: Daicel Chemical Industries, Ltd. (JP)

( * ) Notice: Subject to any disclaimer, the term of this patent is extended or adjusted under 35 U.S.C. 154(b) by 0 days.

(21) Appl. No.: 10/079,631

(22) Filed: Feb. 19, 2002

(65) Prior Publication Data

US 2003/0157033 A1 Aug. 21, 2003

(30) Foreign Application Priority Data

Feb. 19, 2002 (JP) ........................................ 2001-042347

(51) Int. Cl.$^7$ ........................... A61K 7/16; A61K 6/083; C08F 16/16; C08F 222/06
(52) U.S. Cl. ........................... 424/49; 526/271; 526/272
(58) Field of Search ...................... 424/49–58

(56) References Cited

U.S. PATENT DOCUMENTS

| | | | | |
|---|---|---|---|---|
| 4,022,880 A | | 5/1977 | Vinson et al. ................. | 424/49 |
| 4,515,772 A | | 5/1985 | Parran, Jr. et al. ............ | 424/57 |
| 4,627,977 A | | 12/1986 | Gaffar et al. ................. | 424/52 |
| 4,948,848 A | * | 8/1990 | Tazi et al. .................... | 526/78 |
| 4,962,185 A | * | 10/1990 | Tazi et al. ................... | 528/497 |
| 5,003,014 A | * | 3/1991 | Tazi et al. .................... | 526/78 |
| 5,008,355 A | * | 4/1991 | Tazi et al. ................... | 526/271 |
| 5,034,487 A | * | 7/1991 | Tazi et al. ................... | 526/271 |
| 5,202,112 A | | 4/1993 | Prencipe et al. .............. | 424/52 |
| 5,334,375 A | | 8/1994 | Nabi et al. .................... | 424/52 |
| 5,900,470 A | * | 5/1999 | Prosise et al. .............. | 526/272 |
| 5,939,506 A | * | 8/1999 | Plochocka .................. | 526/272 |
| 6,046,291 A | * | 4/2000 | Zhang et al. ................ | 526/272 |
| 6,184,325 B1 | * | 2/2001 | Plochocka .................. | 526/332 |
| 6,211,318 B1 | * | 4/2001 | Plochocka .................. | 526/271 |
| 6,315,987 B1 | * | 11/2001 | Plochocka .................... | 424/49 |
| 6,365,691 B1 | * | 4/2002 | Biss et al. ................... | 526/272 |
| 6,451,944 B2 | * | 9/2002 | Biss et al. ................... | 526/271 |
| 6,464,961 B2 | * | 10/2002 | Plochocka ..................... | 424/48 |

FOREIGN PATENT DOCUMENTS

| | | | | |
|---|---|---|---|---|
| EP | 0 161 898 B1 | 11/1990 | ............ | A61K/7/16 |
| EP | 0 161 899 B1 | 8/1991 | ............ | A61K/7/16 |
| WO | WO 92/02564 | * 2/1992 | ............ | C08F/16/16 |

* cited by examiner

Primary Examiner—Shep Rose
(74) Attorney, Agent, or Firm—Morgan & Finnegan, LLP

(57) ABSTRACT

It was found that if a copolymer of maleic acid or maleic anhydride with an alkyl vinyl ether, which has a specific viscosity of 3.5 or more, is used as an antibacterial-enhancing agent, the action of an antibacterial agent in an oral composition is enhanced and the effect such as adhesion prevention of a soft deposit is improved.

7 Claims, No Drawings

COMPOSITION FOR ORAL CARE

FIELD OF THE INVENTION

The present invention relates to an oral composition. In particular, it relates to an antibacterial antiplaque oral composition useful for toothpaste.

More specifically, it relates to an oral composition containing an antibacterial agent effective to inhibit plaque, and an antibacterial-enhancing agent used therefor, which is a toothpaste composition containing a substantially water-insoluble noncationic antibacterial agent (NAA), and a copolymer of maleic acid or maleic anhydride with an alkyl vinyl ether operative as an antibacterial-enhancing agent (AEA) to enhance the antibacterial antiplaque activity of the NAA.

BACKGROUND OF THE INVENTION

As described in Japanese Patent Application Laid-open No. Hei 6-192060, unlike calculus which is a hard calcified deposit on tooth surface, dental plaque is a soft deposit that forms on any part from the tooth surface to soft oral tissue surface adjacent thereto, especially at the gingival margin. It is said that the plaque such as the soft deposit causes the occurrence of gingivitis. Moreover, the deposit of plaque appears to other persons as a dirt on the tooth so that they may find it unsightly and filthy during face-to-face conversation.

Accordingly, it is highly desirable to include in oral compositions, which are a composition for drugs and materials used in the oral cavity such as toothpaste, antibacterial agents having a function capable of reducing plaque, especially substantially water-insoluble noncationic antibacterial agents such as triclosan (namely, 2,4,4'-trichloro-2'-hydroxydiphenyl ether).

In U.S. Pat. No. 4,022,880 to Vinson et al, though it does not relate to an antiplaque agent, a compound providing zinc ions as an anticalculus agent is admixed with the same antibacterial agent as described above, a wide variety of antibacterial agents which are disclosed, including noncationic compounds such as halogenated salicylanilides and halogenated hydroxydiphenyl ethers.

The combination of the noncationic antibacterial antiplaque halogenated polyhydroxydiphenyl ether, triclosan, with zinc citrate trihydrate has been disclosed in European Patent (EP) Publication 0161,899 to Saxton et al, or in many other publications.

Triclosan is also disclosed in EP Publication 0271,332 to Davis as a toothpaste component containing a solubilizing agent such as propylene glycol.

Further, German Patent Disclosure DE 3,532,860 discloses triclosan in combination with a copper compound.

Still further, EP Publication 0278,744 discloses the combination of triclosan with a potassium-containing tooth desensitizing agent, while EP 0161,898 discloses triclosan as an antiplaque agent in a dentifrice formulated to contain a lamellar liquid crystal surfactant phase.

As described above, several of the commonly known publications related to prior patent applications disclose a combination of triclosan as one effective component of an oral composition with other component. Moreover, in several of these commonly known publications, it is shown that the antiplaque effectiveness of an antibacterial agent such as triclosan exemplified as one component of oral compositions is enhanced by including in the composition an antibacterial-enhancing agent which enhances the preferable delivery of the antibacterial agent to, and retention thereof on, oral surfaces.

In the specification of U.S. patent application Ser. No. 07/738,766, now U.S. Pat. No. 5,202,112, there are described toothpaste and dental gel compositions which contain an amount of a synthetic linear viscoelastic cross-linked polymeric thickening agent, especially a cross-linked methyl vinyl ether/maleic anhydride copolymer, effective to render the oral composition linearly viscoelastic, and a method of promoting oral hygiene by applying an effective amount of the composition to dental surfaces.

On the other hand, the above-described Japanese Patent Application Laid-open No. Hei 6-192060 describes that the antiplaque effectiveness of NAA's such as triclosan in oral compositions is still further enhanced by including in the compositions as an AEA one or a mixture of the synthetic cross-linked polymer, and that such inclusion in dentifrices such as toothpaste and dental gel compositions is preferable.

In the above-described conventionally publicly-known prior arts, when NAA and AEA are used in combination, a sufficient antibacterial antiplaque property can be obtained. However, an effective application of these compositions onto dental surfaces cannot be attained, and therefore still further improvement has been desired as a component for teeth surface application or as a composition.

Accordingly, the object of the present invention is to enhance the application effect to be more preferable state, and to provide more preferable combination of an antibacterial agent and an antibacterial enhancing agent.

In order to overcome the above-described problems, the present inventors have made an extensive research on an oral composition that is harmless to oral surfaces. As a result, the present inventors have found that an oral composition is effective comprising a substantially water insoluble noncationic antibacterial agent used in an effective antiplaque amount, and a specific antibacterial-enhancing agent in an amount effective to enhance delivery of the antibacterial agent to, and the retention thereof on, the oral surfaces, wherein the specific antibacterial-enhancing agent comprises a synthetic polymer of maleic acid or maleic anhydride with an alkyl vinyl ether which has a specific viscosity of 3.5 or more. The present invention has been accomplished based on this finding.

SUMMARY OF THE INVENTION

The subject matter of the invention will be described hereinbelow.

A first aspect of the present invention relates to an oral composition comprising an antibacterial agent and an antibacterial-enhancing agent, the antibacterial-enhancing agent being a copolymer of maleic acid or maleic anhydride with an alkyl vinyl ether, in which the copolymer has a specific viscosity of 3.5 or more.

A second aspect of the present invention relates to an oral composition according to the first aspect of the invention, in which the alkyl vinyl ether is methyl vinyl ether.

A third aspect of the present invention relates to an oral composition according to the first aspect of the invention, in which the specific viscosity of the copolymer of maleic acid or maleic anhydride with an alkyl vinyl ether is 3.8 to 5.2.

A fourth aspect of the present invention relates to an oral composition according to the first aspect of the invention, in which the copolymer of maleic acid or maleic anhydride with an alkyl vinyl ether is used in an amount of 0.1 to 2.5% by weight.

A fifth aspect of the present invention relates to an oral composition according to the first aspect of the invention, in which the antibacterial agent is a noncationic antibacterial agent.

A sixth aspect of the present invention relates to an oral composition according to the fifth aspect of the invention, in which the noncationic antibacterial agent is triclosan.

A seventh aspect of the present invention relates to an oral composition according to any one of the first to sixth aspects of the invention, in the form of a toothpaste, a liquid toothpaste, a dental gel or a mouthwash.

DETAILED DESCRIPTION OF THE INVENTION

All the substantially water insoluble noncationic antibacterial agents (NAA) which are disclosed in the above-described prior arts, are effectively used in the present invention.

In the present invention, NAA can be used alone and also in combination of two or more thereof. Further, it can be used together with other components that do not affect the action and effect of NAA. The effective ratio of NAA used is, in an effective antiplaque amount, preferably from about 0.01 to 5% by weight, more preferably from about 0.03 to 1% by weight, still more preferably from about 0.25 to 0.5% by weight and most preferably from about 0.25 to 0.35% by weight, in the oral composition comprising the NAA and an antibacterial-enhancing agent described later as another essential component.

For example, the NAA is used in an amount of about 0.3% by weight in a dentifrice such as toothpaste, dental gel or the like, and it is used in an amount of from about 0.03 to 0.3% by weight, more preferably from about 0.03 to 0.1% by weight in a mouthwash or a liquid dentifrice.

The NAA used is substantially water-insoluble and the term "water-insoluble" as used herein means that the solubility of the NAA is less than about 1% by weight in water at 25° C. and is in actuality even less than about 0.1% by weight.

Examples of the NAA according to the present invention include the phenolic compounds such as thymol, eugenol, hexyl resorcinol and 2,2-methylene bis(4-chloro-6-bromophenol) or triclosan. Of these, triclosan is preferable.

In the oral composition according to the present invention, the AEA as another essential component comprises a copolymer of maleic acid or maleic anhydride with an alkyl vinyl ether, which is preferably used in an amount of about 0.02 to 5% by weight, more preferably about 0.1 to about 2.5% by weight in the oral composition of the present invention. The polymer used has a higher molecular weight than that of the conventional one and its specific viscosity is preferably 3.5 or higher, more preferably 3.8 to 5.2.

Preferable examples of the above-described copolymer having a higher specific viscosity include VEMA A106H (a specific viscosity: 4.0) or VEMA A106H5 (a specific viscosity: 4.5), which is a copolymer of maleic anhydride with methyl vinyl ether, produced by Daicel Chemical Industries, Ltd., and those are easily available.

Incidentally, examples of the conventionally used copolymer with a low specific viscosity include one having a specific viscosity of 1.0 (AN139 produced by Gantrez, which is a copolymer of maleic anhydride with methyl vinyl ether), one having a specific viscosity of 0.3 (AN119 produced by Gantrez, which is a copolymer of maleic anhydride with methyl vinyl ether; VEMA A101 produced by Daicel Chemical Industries, Ltd.), one having a specific viscosity of 1.0 (VEMA A103 produced by Daicel Chemical Industries, Ltd.) and one having a specific viscosity of 3.0 (S-97 produced by GAF Corporation, which is a copolymer of maleic anhydride with methyl vinyl ether; VEMA A106 produced by Daicel Chemical Industries, Ltd.).

As described above, the copolymer of maleic anhydride with an alkyl vinyl ether according to the present invention, which has a high specific viscosity, is used preferably within the range of 0.02 to 5% by weight, more preferably of 0.1 to about 2.5% by weight. It is found that such usage enables the desired effect, more specifically, a preferable delivery of triclosan to, and retention thereof on, oral surfaces, and that the difference is large in the obtained effect between AEA having a high specific viscosity and AEA having a low specific viscosity.

The oral compositions according to the present invention have excellent stability against phase separation or syneresis, viscosity change in storage, and settling of dissolved, dispersed or suspended particles under high and low temperature conditions, freedom from fish eyes, excellent texture and other cosmetic properties, ease of extrusion from a dispensing tube, pump or the like (easily shear thinned), good stand-up after extrusion (quick recovery of structure), and fluoride ion availability to dental enamel-like substances leading to improved anti-caries effects.

The oral composition according to the present invention will retain sufficient energy when a stress or strain is applied, at least over the extent expected to be encountered for products of this type, for example, when squeezed out of a toothpaste tube or pump to return to its previous condition and exhibit excellent stand-up when the stress or strain is removed.

In the polymer having the same structure unit, as the molecular weight becomes higher, a value of the specific viscosity as described in the present invention becomes greater. Therefore, the specific viscosity is widely used as the standard relatively indicating a molecular weight of polymer, and the specific viscosity used in the present invention essentially means the same thing as the molecular weight.

The measuring method of the specific viscosity is shown below.

In methyl ethyl ketone which is a solvent, a copolymer as an object of measuring is dissolved to prepare a solution having a concentration of 1% (weight/volume %, at 25° C.). By using a capillary viscometer prescribed by JIS K6726, the copolymer solution obtained is measured on the falling time at 25° C., and the specific viscosity is calculated by the following formula: specific viscosity=(A−B)/B. In the above-described formula, A=a measured value on falling time of copolymer solution, B=a measured value on falling time of the solvent only.

It is needless to mention that the toothpaste or the like as an oral agent according to the present invention may have an anticalculus property in addition to the above-described antiplaque property, and an effective anticalculus amount of an anticalculus agent is desirably included in these oral compositions. An anticalculus agent as described herein typically includes linear, molecularly dehydrated (generally water soluble or synthetic) polyphosphates and preferred examples thereof include hexametaphosphates, tripolyphosphates and pyrophosphates.

As described in Japanese Patent Application Laid-open No. Hei 6-192060 above, U.S. Pat. No. 4,515,772 to Parran et al discloses oral anticalculus compositions containing a fluoride ion source and soluble dialkali metal pyrophosphates alone or admixed with tetraalkali metal pyrophosphates. U.S. Pat. No. 4,627,977 to Gaffar et al discloses oral compositions containing the above-described preferred polyphosphate anticalculus agents in combination with a fluoride and a polycarboxylate to inhibit enzymatic hydrolysis of the polyphosphate in saliva. Such polycarboxylates, when cross-linked, are operative herein as AEA's.

The linear molecularly dehydrated polyphosphates are generally employed in the form of their wholly or partially neutralized water soluble or readily water dispersible alkali metal (e.g. sodium or potassium) salts or ammonium salts, or any mixtures thereof. Representative examples include sodium hexametaphosphate, sodium tripolyphosphate, disodium diacid, trisodium monoacid, tetrasodium pyrophosphates, the corresponding potassium salts and the like. Especially desirable are the tetraalkali metal pyrophosphates such as tetrasodium pyrophosphate (TSPP), tetrapotassium pyrophosphate (TKPP) or mixtures thereof, especially mixtures with a relatively large content of TKPP. These polyphosphate anticalculus agents, when employed in oral compositions of the present invention, are used in approximate weight amounts of 0.1 to 7% by weight, typically 0.1 to 3% by weight, usually 2% by weight.

The sources of fluoride ions, or fluoride ion-providing compounds, when employed herein as an inhibitor of enzymatic hydrolysis of polyphosphate anticalculus agents and/or as anti-caries agents are well known. These compounds may be slightly soluble in water or may be fully water-soluble. They are characterized by their ability to release fluoride ions into water and by freedom from undesired reactions with other compounds of the oral preparation.

Examples of these compounds include inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, sodium monofluorophosphate, aluminum mono-or difluorophosphate, and fluorinated sodium calcium pyrophosphate. Among these, alkali metal and tin fluorides, such as sodium and stannous fluorides, sodium monofluorophosphate (MFP) and mixtures thereof, are preferred.

The amount of the fluoride-providing compound used is dependent to some extent upon the type of compound, its solubility, the type of oral preparation and the like, but it is said that generally it must be about 0.005 to about 3.0% by weight in the preparation. Needless to say, it must be a nontoxic amount.

In a dentifrice preparation, e.g. dental gel, toothpaste (including cream), toothpowder, or dental tablet, an amount of such compound which releases up to about 5,000 ppm of fluorine ion by weight of the preparation is considered preferable. Any suitable minimum amount of such compound may be used, but it is preferable to employ sufficient amount of compound to release about 300 to 2,000 ppm, more preferably about 800 to about 1,500 ppm of fluoride ion. Typically, in the cases of alkali metal fluorides and stannous fluoride, this compound is present in an amount of up to about 2% by weight, based on the weight of the preparation, and preferably in the range of about 0.05 to 1% by weight. The compound may be present preferably in an amount of from about 0.1 to 3% by weight, more typically about 0.76% in the form of sodium monofluorophosphate (MFP) and from about 0.005 to 1% by weight, more typically about 0.243% by weight in the form of sodium fluoride (NaF).

In certain other desirable forms of the oral composition according to the present invention, for example, the oral composition may be substantially solid or pasty such as toothpowder, a dental tablet, a toothpaste, dental gel or cream.

The vehicle of such solid or pasty oral preparations generally contains polishing materials. Examples of the polishing materials include water-insoluble sodium metaphosphate, potassium metaphosphate, tricalcium phosphate, dihydrated calcium phosphate, anhydrous dicalcium phosphate, dihydrated calcium phosphate, anhydrous pyrophosphate, magnesium orthophosphate, trimagnesium phosphate, calcium carbonate, aluminum silicate, zirconium silicate, silica, bentonite, and mixtures thereof.

Other suitable polishing materials include particulate thermosetting resins described in U.S. Pat. No. 3,070,510 of Dec. 15, 1962 such as melamine-formaldehydes, phenol-formaldehydes, urea-formaldehydes, and cross-linked poly-epoxides and polyesters.

Among these, preferred polishing materials include crystalline silica having particle sizes of about 5 $\mu$m or less, a mean particle size of about 1.1 $\mu$m or less and a surface area of about 50,000 cm/g or less, silica gel or colloidal silica, and an amorphous alkali metal alumino-silicate complex.

When visually clear gels are employed, a polishing material such as colloidal silica and alkali metal alumino-silicate complexes, for example Syloid 72 and Syloid 74 (trademark: SYLOID) or Santcel 100 (trademark: SANTCEL) is particularly useful, since they have refractive indices close to those of gelling agent-liquid (including water and/or humectant) systems commonly used in dentifrices.

Many of the so-called "water-insoluble" polishing materials are anionic in character and also include small amounts of soluble materials. Insoluble sodium metaphosphate may be formed in any suitable manner as illustrated by Thorpe's Dictionary of Applied Chemistry, Volume 9, 4th Edition, pp. 510–511.

The forms of insoluble sodium metaphosphate known as Madrell's salt and Kurrol's salt are further examples of suitable materials.

These metaphosphate salts exhibit only a minute solubility in water and therefore are commonly referred to as insoluble metaphosphates (IMP). There is present therein a minor amount of soluble phosphate material as impurities, usually a few percent by weight such as up to 4% by weight. A soluble phosphate material, which is believed to include a soluble sodium trimetaphosphate in the case of insoluble metaphosphate, should be reduced or eliminated by washing with water. The insoluble alkali metal metaphosphate is typically employed in powder form of a particle size such that no more than about 1% by weight of the material is larger than about 37 $\mu$m.

The polishing material is generally present in the solid or pasty compositions in weight concentrations of about 10 to about 99% by weight. Preferably, it is present in amounts ranging from about 10 to about 75% by weight in toothpaste, and from about 70 to about 99% by weight in toothpowder.

In a toothpaste, the liquid vehicle may comprise water and humectant typically in an amount ranging from about 10 to about 90% by weight of the preparation. Specific examples of the suitable humectants/carries include glycerine, propylene glycol, polyethylene glycol (e.g. polymerization degree: 400–600), and the like. Liquid mixtures of water, glycerine and sorbitol can also be used. In clear gels where the refractive index is an important consideration, a mixture containing from about 3 to 30% by weight of water, from 0 to about 80% by weight of glycerine, and from about 20 to 80% by weight of sorbitol is preferably employed.

Other conventional thickeners (binding, gelling agents) may be included in these dentifrice compositions, usually in amounts ranging from about 0.1 to about 4 parts by weight based on 1 part by weight of the defined cross-linked polymeric thickener.

Examples of such other thickeners include xanthan gum, hydroxyethyl cellulose and water-soluble salts of cellulose ether such as sodium carboxymethyl cellulose and sodium carboxymethyl hydroxyethyl cellulose. Further, natural gums such as carrageenan (Irish moss, Viscarin), gum karaya, gum Arabic, and gum tragacanth can also be used. In addition, colloidal magnesium aluminum silicate, Veegum or finely divided silica can be used as part of the thickening agent system. Preferred thickening agents include xanthan gum, carrageenan, sodium carboxymethyl cellulose, sodium carboxymethyl hydroxyethyl cellulose and hydroxyethyl cellulose, preferably in proportions of from about 0.4 to about 3 parts per part of the cross-linked polymeric thickener.

Also useful is synthetic hectorite, a synthetic colloidal magnesium alkali metal silicate complex clay available for example as Laponite (e.g. CP, SP 2002, D) marketed by Laporte Industries Limited. The analysis results of Laponite D show, by weight, 58.00% $SiO_2$, 25.40% MgO, 3.05% $Na_2O$, 0.98% $Li_2O$, and some water and trace metals. The specific gravity of this substance is 2.53 and it has an apparent bulk density (g/ml at 8% moisture) of 1.0.

Other suitable thickeners include starch, polyvinylpyrrolidone, hydroxybutyl methyl cellulose, hydroxypropyl methyl cellulose, alginates, gum ghatti, locust bean gum, pectins, and tamarind gum and the like.

The oral preparations are usually to be sold in suitable labeled packages or in other form. Thus a jar of mouthrinse will have a label describing it, in substance, as a mouthrinse or mouthwash and having directions for its use, and a toothpaste, cream or gel will usually be in a collapsible tube typically aluminum, lined lead or plastic, or other squeeze, pump or pressured dispenser for metering out the contents, having a label describing it, in substance, as a toothpaste, gel or dental cream.

In the composition according to the present invention, organic surface-active agents are used as composition components to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties.

Suitable examples of anionic surfactants are given as below: water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonates, and the substantially saturated higher aliphatic acyl amides of lower aliphatic amino carboxylic acid compounds, such as those having 12 to 16 carbons in the fatty acid, alkyl or aryl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material.

The use of these sarcosinate compounds in the oral compositions according to the present invention is particularly advantageous since these materials exhibit a prolonged and marked effect in the inhibition of acid formation in the oral cavity due to breakdown of carbohydrate in addition to enabling some reduction in the solubility of tooth enamel-like substances in acid solutions.

Examples of water-soluble nonionic surfactants are condensation products of ethylene oxide with various active hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic PE6100, produced by BASF).

Various other materials may be incorporated as adjuvants in the oral preparations of this invention such as whitening agents, preservatives, silicones, chlorophyll compounds, other anticalculus agents, and/or ammoniated material such as urea, diammonium phosphate, and mixtures thereof. These adjuvants, when added, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenylalanine methyl ester), saccharine and the like. When used, flavoring and sweetening materials are added such that they individually or together comprise up to about 0.1 to 5% by weight of the preparation.

An oral composition according to this invention when used as a mouthwash or dentifrice is applied regularly to the oral cavity as by "swishing or brushing" dental surfaces, such as every second or third day or preferably from 1 to 3 times daily, at a pH of about 4.5 to about 10, generally about 5.5 to about 9, preferably about 6 to 8, for at least 2 weeks up to 8 weeks or more up to lifetime. The composition is typically removed by rinsing with water after each application.

EXAMPLES

Examples 1—1 to 1–8, Comparative Examples 1—1 to 1–3

Various Examples using the composition according to the present invention will be illustrated. The copolymer is hydrolyzed in water for 2 to 3 days at an appropriate solid concentration of from about 5 to 10% by weight in copolymer content, neutralized to a pH of 7, the mixture is dispersed in the humectant system, and the other dentifrice ingredients are mixed with the obtained dispersion having a pH of about 7.

Following known and scientifically-recognized procedures, hydroxyapatite (HA), the inorganic phase of tooth enamel-like substances, was used as an in vitro experimental model for human teeth to evaluate the effect of the cross-linked polymer on the delivery and retention of triclosan to tooth surfaces. HA disk was coated with saliva to form a salivary thin layer on the disk. The disk was used instead of HA powder which has a very high surface area and does not simulate in vivo surface to volume ratios. Dentifrice liquid phase solution containing triclosan (the content of the oral composition is shown in Table 1) with and without an antibacterial-enhancing agent was made with all the components of dentifrice except abrasive and employed for Examples and Comparative Examples. In Table 1, the amount of the antibacterial-enhancing agent used was expressed by X. The X used here is the same as X in Table 2. In Table 2, triclosan uptake results (triclosan uptake weight µg/disk, expressed by the average value of n=3) are shown.

In Table 2, VEMA A106H and VEMA A106H5 are polymers as an antibacterial-enhancing agent, each corresponding to a copolymer of maleic anhydride with methyl vinyl ether having a specific viscosity of 4.5 and 4.0, respectively. As a copolymer of maleic anhydride with methyl vinyl ether in Comparative Examples, 2 parts by weight of Gantrez S-97 (a specific viscosity: 3.0) is used and 2 parts by weight of VEMA A106 (a specific viscosity: 3.0) is similarly used.

TABLE 1

Composition of Dentifrice Liquid Phase Solution

| Ingredients | Parts by weight |
|---|---|
| Sorbitol (70% by weight aqueous solution) | 30.0 |
| Glycerol | 9.5 |
| Propylene Glycol | 0.5 |
| Sodium Lauryl Sulfate | 2.0 |
| Copolymer (antibacterial-enhancing agent) | X |
| Flavor Oil | 0.95 |
| Triclosan (antibacterial agent) | 0.3 |
| Water | 55.257 |

*The dentifrice liquid phase solution was adjusted to a pH of 6.5 by adding 50% by weight of NaOH solution.

TABLE 2

Examples and Comparative Examples

| | Copolymer X % | Parts by weight | Triclosan Uptake µg/Disk; n = 3 |
|---|---|---|---|
| Example | | | |
| 1-1 | VEMA A106H5 | 0.1 | 124 ± 5 |
| 1-2 | VEMA A106H5 | 0.3 | 138 ± 6 |
| 1-3 | VEMA A106H5 | 0.5 | 145 ± 6 |
| 1-4 | VEMA A106H5 | 0.75 | 163 ± 7 |
| 1-5 | VEMA A106H | 0.1 | 117 ± 5 |
| 1-6 | VEMA A106H | 0.3 | 127 ± 6 |
| 1-7 | VEMA A106H | 0.5 | 138 ± 6 |
| 1-8 | VEMA A106H | 0.75 | 149 ± 7 |
| Comparative Example | | | |
| 1-1 | None | | 33 ± 4 |
| 1-2 | Gantrez S-97 | 2 | 90 ± 5 |
| 1-3 | VEMA A106 | 2 | 93 ± 6 |

As is apparent from the results in Table 2, it is verified that even when only 0.1 part by weight of a highly-polymerized copolymer of maleic anhydride with an alkyl vinyl ether is used, the uptake of triclosan from dentifrice liquid phase solution to saliva-coated HA disk is enhanced by 3.5 to 3.8 fold compared to the case where an antibacterial-enhancing agent is not contained, and is also enhanced by 1.3 to 1.4 fold compared to the case where 2 parts by weight of Gantrez S-97 or VEMA A106 that is not highly-polymerized is used.

The result shown in Table 2 further verify that the uptake of triclosan to saliva-coated HA disk is further enhanced with increased concentration of highly-polymerized VEMA.

Examples 2 to 7

Dentifrice compositions (Table 3) and mouthwash compositions (Table 4), which are other compositions comprising the oral composition according to the present invention, are shown below.

TABLE 3

Dentifrice Compositions (Parts by weight)

| Ingredients | Example 2 | Example 3 | Example 4 | Example 5 |
|---|---|---|---|---|
| Sorbitol (70% aqueous solution) | 20.0 | 20.0 | 20.0 | 20.0 |
| Glycerol | 10.0 | 22.0 | 10.0 | 10.0 |
| Propylene Glycol | 0.5 | 0.5 | 0.5 | 0.5 |
| Iota Carrageenan | 0.75 | 0.75 | 0.75 | 0.75 |
| Na Saccharin | 0.3 | 0.3 | 0.3 | 0.3 |
| MFP*1 | 0.76 | 0.76 | 0.76 | 0.76 |
| TiO$_2$ | 0.5 | 0.5 | 0.5 | 0.5 |
| VEMA A106H5 | 0.3 | 0.3 | 0.3 | 0.3 |
| Zeodent113*2 | 20.0 | 20.0 | 20.0 | |
| Sylodent15*3 | 3.0 | 3.0 | 3.0 | |
| Alumina4Baco*4 | | | | 8.0 |
| Af230 Flavor Oil | 0.95 | 0.95 | 0.95 | 0.95 |
| SLS*5 | 2.0 | 2.0 | 2.0 | 2.0 |
| Triclosan | 0.3 | 0.3 | 0.3 | 0.3 |
| TSPP*6 | 2.0 | — | — | — |

*The composition values of the compositions are indicated by part by weight and water is added such that it comprises 100 parts by weight as a whole.
*1 to 6 are shown below.
*1 Sodium monofluorophosphate (replaceable by 0.243 NaF)
*2 Silica polishing material
*3 Silica thickener
*4 Polishing material
*5 Sodium lauryl sulfate
*6 Tetrasodium pyrophosphate

TABLE 4

Mouthwash

| Ingredients | Example 6 Parts by weight | Example 7 Parts by weight |
|---|---|---|
| TAPP | 2.00 | — |
| VEMA A106H5 | 0.1 | 0.1 |
| Glycerol | 10.00 | 10.00 |
| Propylene Glycol | 5.00 | 5.00 |
| Sodium Fluoride | 0.05 | 0.05 |
| PluronicF10*7 | 1.0 | 1.0 |
| Triclosan | 0.10 | 0.10 |
| Flavor | 0.40 | 0.40 |

*The composition values of the compositions are indicated by part by weight and water is added such that it comprises 100 parts by weight as a whole.
*7 Polyoxyethylene/polyoxypropylene block copolymer As is apparent from the description above, in the blend of an antibacterial agent and an antibacterial-enhancing agent which is a copolymer of maleic acid or maleic anhydride with an alkyl vinyl ether, if an antibacterial-enhancing agent comprising a copolymer having a high specific viscosity of 3.5 or more is used, the action of antibacterial agent on tooth is enhanced so that formation of a soft deposit can be effectively prevented.

What is claimed is:

1. An oral composition comprising an antibacterial agent and an antibacterial-enhancing agent, wherein the antibacterial-enhancing agent is a copolymer consisting essentially of maleic acid or maleic anhydride and an alkyl vinyl ether, and the copolymer has a specific viscosity of 3.5 or more.

2. An oral composition according to claim 1, wherein the alkyl vinyl ether is methyl vinyl ether.

3. An oral composition according to claim 1, wherein the specific viscosity of the copolymer is 3.8 to 5.2.

4. An oral composition according to claim 1, wherein the copolymer is used in an amount of 0.1 to 2.5% by weight.

5. An oral composition according to claim 1, wherein the antibacterial agent is a noncationic antibacterial agent.

6. An oral composition according to claim 5, wherein the noncationic antibacterial agent is tricolsan.

7. A product comprising the oral composition according to one of claims 1 to 6, wherein said product is selected from the group consisting of toothpaste, a liquid toothpaste, a dental gel and a mouthwash.

* * * * *